United States Patent
Pellico

(10) Patent No.: US 9,993,533 B2
(45) Date of Patent: Jun. 12, 2018

(54) USE OF HYDROLYTIC AND OXIDATIVE ENZYMES TO DISSOLVE BIOFILM IN AIRWAY PASSAGES

(71) Applicant: Laclede, Inc., Rancho Dominguez, CA (US)

(72) Inventor: Michael Pellico, Los Angeles, CA (US)

(73) Assignee: Laclede, Inc., Rancho Dominguez, CA (US)

( * ) Notice: Subject to any disclaimer, the term of this patent is extended or adjusted under 35 U.S.C. 154(b) by 14 days.

(21) Appl. No.: 14/991,571

(22) Filed: Jan. 8, 2016

(65) Prior Publication Data

US 2016/0144004 A1    May 26, 2016

Related U.S. Application Data

(63) Continuation of application No. 12/667,977, filed as application No. PCT/US2008/051819 on Jan. 23, 2008, now abandoned.

(60) Provisional application No. 60/948,343, filed on Jul. 6, 2007.

(51) Int. Cl.
| | |
|---|---|
| *A61K 38/40* | (2006.01) |
| *A61K 38/47* | (2006.01) |
| *A61K 38/54* | (2006.01) |
| *A61K 38/44* | (2006.01) |
| *A61K 45/06* | (2006.01) |
| *A61K 31/573* | (2006.01) |
| *A61K 38/46* | (2006.01) |

(52) U.S. Cl.
CPC ............ *A61K 38/54* (2013.01); *A61K 31/573* (2013.01); *A61K 38/40* (2013.01); *A61K 38/44* (2013.01); *A61K 38/443* (2013.01); *A61K 38/465* (2013.01); *A61K 38/47* (2013.01); *A61K 45/06* (2013.01); *C12Y 111/01007* (2013.01); *C12Y 302/01* (2013.01); *C12Y 302/01011* (2013.01); *C12Y 302/01015* (2013.01); *C12Y 302/01017* (2013.01)

(58) Field of Classification Search
CPC .......... A61K 38/47; A61K 38/40; A61K 8/22; A61K 33/40; A61K 8/66; C12Y 302/01017

See application file for complete search history.

(56) References Cited

U.S. PATENT DOCUMENTS

| | | |
|---|---|---|
| 6,100,080 A | 8/2000 | Johansen |
| 6,799,585 B2 | 10/2004 | Lengling et al. |
| 6,812,196 B2 | 11/2004 | Rees et al. |
| 6,838,050 B1 | 1/2005 | Green et al. |
| 2002/0037260 A1 | 3/2002 | Bundy et al. |
| 2004/0101560 A1 | 5/2004 | Sawchuk et al. |
| 2004/0202670 A1 | 10/2004 | Apicella |
| 2005/0249695 A1 | 11/2005 | Tiller et al. |
| 2006/0051384 A1 | 3/2006 | Scholz et al. |
| 2006/0121019 A1 | 6/2006 | Bundy et al. |
| 2006/0204452 A1 | 9/2006 | Velamakanni et al. |
| 2007/0049641 A1 | 3/2007 | Tirouvanziam et al. |
| 2008/0031868 A1 | 7/2008 | An |

FOREIGN PATENT DOCUMENTS

| | | |
|---|---|---|
| WO | 199106308 | 5/1991 |
| WO | 199826807 | 6/1998 |
| WO | 200193875 | 12/2001 |
| WO | 2004064732 | 8/2004 |
| WO | 2007067520 | 6/2007 |

OTHER PUBLICATIONS

Moslemi, M "Relationship of Salivary Lactoferrin and Lysozyme Concentrations with Early Childhood Caries" J Dent Res Dent Clin Dent Prospect, 2015; 9(2):109-114 | doi: 10.15171/joddd.2015. 022.*

Organz, B et al., "Bacterial biofilm removal using fungal enzymes." Enzyme and Microbial Technology (2006) 40(1): 51-56.

Del Pozo J L et al., "The challenge of treating biofilm associated bacterial infections." Clinical Pharmacology and Therapeutics (2007) 82(2): 204-209.

\* cited by examiner

*Primary Examiner* — Christopher R Tate
*Assistant Examiner* — Aaron J Kosar
(74) *Attorney, Agent, or Firm* — Lewis Kohn & Walker LLP; David M. Kohn

(57) ABSTRACT

A composition for removal of biofilm in the airway passage is useful for the treatment of infections such as pneumonia cause by *Mycoplasma pneumoniae*. In general, the composition comprises: (1) a quantity of at least one enzyme that catalyzes the hydrolysis of a bond that connects two monosaccharides in a polysaccharide or that connects a monosaccharide with a protein molecule in a glycoprotein sufficient to break down biofilm in the airway; and (2) a pharmaceutically acceptable carrier suitable for administration into the airway. The composition can further include ingredients such as a steroid, lysozyme, lactoferrin, or a peroxidase; if a peroxidase is included, the composition can further include an oxidase to generate peroxide as well as a substrate for the oxidase. The composition can be used in methods for treatment of an infection based on the ability of the composition to dissolve biofilm in the airway.

18 Claims, No Drawings

USE OF HYDROLYTIC AND OXIDATIVE ENZYMES TO DISSOLVE BIOFILM IN AIRWAY PASSAGES

CROSS-REFERENCES

This application is a Continuation of U.S. National Stage application Ser. No. 12/667,977 filed Jan. 6, 2010, which claims priority under 35 U.S.C. 371 from International Patent Application No. PCT/US2008/51819 filed Jan. 23, 2008, which claims the benefit of priority from Provisional Application Ser. No. 60/948,343 filed Jul. 6, 2007, the entire contents of which are herein incorporated by reference.

FIELD OF THE INVENTION

This invention relates to airway treatment compositions where the treatment composition contains biofilm dissolving enzymes, in particular hydrolytic enzymes and oxidative enzymes.

BACKGROUND OF THE INVENTION

Today, ventilator-induced pneumonia is one of the leading causes of hospital deaths due to infections. Such infections are frequently referred to as nosocomial infections.

*Mycoplasma pneumoniae* is resistant to many antibiotics such as penicillin, cephalosporins, and vancomycin. *M. pneumoniae* causes a pneumonia often called "walking pneumonia" or "primary atypical pneumonia."

Other cases of pneumonia can be causes by a number of species of bacteria, including, but not limited to, *Streptococcus* species, *Staphylococcus* species, *Pseudomonas* species, *Haemophilus* species, and *chlamydia*.

The disease of pneumonia can be divided into two forms: bronchial pneumonia and lobar pneumonia.

Multiple antibiotic resistant forms of *Streptococcus pneumonia* that emerged in the early 1970s in Papua New Guinea and South Africa were thought to be flukes, but multiple antibiotic resistance now covers the globe and has rapidly increased since 1985. Increases in penicillin resistance have been followed by resistance to cephalosporins and by multidrug resistance. The incidence of resistance to penicillin increased from <0.02% in 1987 to 3% in 1994 to 30% in some communities in the United States and 80% in regions of some other countries in 1998. Resistance to other antibiotics has emerged simultaneously: 26% resistant to trimethoprim/sulfa, 30% resistant to cefotaxime, 30% resistant to macrolides, and 25% resistant to multiple drugs. Resistant organisms remain fully virulent.

Current treatment for airway infections is still with antibiotics. However the overuse of antibiotics is leading to a proliferation of antibiotic resistant bacteria. It has been known for many years that bacteria have the ability to spread antibiotic resistance from one species to another through the action of plasmids known as resistance transfer factors (RTFs). Of particular significance is the generation of plasmids that carry multiple resistance genes. These mechanisms are described in A. A. Sayers and D. D. Whitt, "Bacterial Pathogenesis: A Molecular Approach" (ASM Press, Washington, D.C. 1994), pp. 107-109, incorporated herein by this reference.

The reason that antibiotics are frequently ineffective in this clinical situation is that recently it has been discovered that bacteria are living in a dormant state inside a slimy biofilm. One example of such a biofilm occurs in the ear. The seemingly innocuous fluid behind the ear is actually a microbe-laden biofilm containing bacteria that become activated and grow rapidly under the right circumstances. This biofilm is also in the outer ear canal.

This revised understanding had come about because, previously, scientists studied bacteria in their free-floating form. Bacteria prefer the slimy, communal life because it protects them from toxins in the environment. Biofilm formation takes place in a step by step manner. First, inorganic or organic molecules are absorbed to a surface. This creates a conditioning layer that increases the ability of bacteria to attach to a surface. Once a conditioning layer is formed, bacterial adhesion follows. Live or dead cells will attach to surfaces with similar propensity. Bacterial attachment is mediated by fimbriae, pili, and flagella, and by extracellular polysaccharides.

When first formed, the bond between the conditioning layer and the bacteria is not strong and can be easily removed. With time however, these bonds are strengthened, making removal difficult. Once embedded within a biofilm, bacterial cells have an opportunity to repair cellular damage and to metabolize nutrients within the biofilm. As the biofilm continues to grow, the extracellular polysaccharides provide more and more protection. A biofilm is mature within 24 hours. Biofilm development can occur within one hour. After an eight-hour period, more than 91% of the bacteria are strongly attached within the biofilm. Killing bacteria within a biofilm requires up to 1000 times more antibiotic than is required to kill free-floating bacteria. The film physically prevents the antibiotic from reaching the bacteria. In addition, most bacteria in the biofilm are dormant and antibiotics typically only kill bacteria that are actively dividing.

Similarly, biofilms occur in the respiratory tract. Airway passages are coated with a slimy reservoir of hibernating bacteria. These inactive bacteria do not cause symptoms of an active infection but eventually they slough off and become free-floating active bacteria and cause another infection. This is one of the significant factors behind the existence of recurrent infections in such patients. Data show that bacteria incorporated in biofilms are more resistant than single cells and this is believed to be caused by physical protection by the biofilm matrix or by altered physiology of bacterial cells in the biofilm.

Bacteria have a natural tendency to attach to surfaces and to initiate the formation of a biofilm. The biofilm matrix is a collection of microcolonies with water channels in between and an assortment of cells and extracellular polymers such as polysaccharides, glycoproteins, and proteins. The different types of bonds between the saccharides give rise to a large number of different classes of polysaccharides including levans, dextrans, cellulose, glycogen, and alginates. Bacteria have the capacity to attach to and to colonize the surface of most materials. Attachment often results in the production of extracellular polysaccharides and changes in cellular morphology and growth rates. Different genes are expressed in bacteria that are attached to surfaces as compared to planktonic bacteria. As a result, surface-attached bacteria display increased resistance to toxic chemicals and biocides. While biocides have proven effective in killing free-floating bacteria, they are not effective in destroying bacteria within a biofilm. It becomes imperative that the biofilm be destroyed before the biocides can become effective.

There are many methods known to remove biofilms. The methods that are used to remove biofilm include the use of hypochlorite, hydrogen peroxide, ozone, detergents, or acids, the application of heat, the use of mechanical activity, or the use of ultrasound. Combinations of these methods are also used.

Many of these methods, although effective, are not suitable for use on biofilms that form on the body or within the body, such as in the respiratory tract. These methods are too harsh and disruptive of tissue for use in this context. A safe method is required to remove biofilms that form on the body or within the body.

Enzymes have been used to dissolve biofilms before, but not in the context of biofilms that form on the body or within the body. In laundry detergents, enzymes are used to remove deposits that may, in fact, be biofilms. Contact lens solutions use enzymes to remove the biofilm that can grow on a contact lens. In the dental field, dextranase and mutanase are used to remove plaque, a biofilm, from teeth.

Accordingly, there is a need for an improved method for removing biofilms that form on the body or within the body, particularly in airway passages. The improved method should be effective and safe. The improved method should also be compatible with antibiotics and other treatments for bacterial infection.

SUMMARY OF THE INVENTION

This invention is directed to compositions that have the activity of removing biofilm, particularly in airway passages. Compositions and methods according to the present invention are suitable for treatment of airway infections.

One aspect of the present invention is a composition for removal of biofilm in airway passages comprising:

(1) a quantity of at least one enzyme that catalyzes the hydrolysis of a bond that connects two monosaccharides in a polysaccharide or that connects a monosaccharide with a protein molecule in a glycoprotein sufficient to break down biofilm in airway passages; and (2) a pharmaceutically acceptable carrier suitable for administration into airway passages.

The at least one enzyme that catalyzes the hydrolysis of a bond that connects two monosaccharides in a polysaccharide or that connects a monosaccharide with a protein molecule in a glycoprotein can be selected from the group consisting of xylanase, β-glucanase, cellulase, α-galactosidase, glucanases, amylase, hyaluronidase, polygalacturonase (pectinase), dextranase, cellobiohydrolase, pullulanase, glycosylceramidase, glucan 1,4-α-glucosidase, oligo-1,6-glucosidase, fucoidanase, glycosylceramidase, thioglucosidase, and glycopeptide N-glycosidase. Typically, the enzyme is selected from the group consisting of xylanase, β-glucanase, cellulase, α-galactosidase, glucanases, amylase, hyaluronidase, polygalacturonase (pectinase), dextranase, and cellobiohydrolase.

The composition can further comprise at least one ingredient in a quantity effective to prevent or inhibit inflammation in the airway passage. This can be a steroid such as hydrocortisone.

The composition can further comprise an antibiotic that is effective in the treatment of M. pneumoniae. Alternatively, the composition can further comprise an antiviral or antifungal agent.

The composition can further include lysozyme or lactoferrin. Additionally, the composition can further include at least one peroxidase in a quantity sufficient to exert a bactericidal action. A suitable peroxidase is lactoperoxidase. When the composition includes a peroxidase, the composition can further include at least one substrate that can be converted to an ion with bactericidal properties by the enzymatic action of the peroxidase in a quantity such that an effective concentration of the ion with bactericidal properties is produced by the catalytic action of the peroxidase. When the composition includes a peroxidase, the composition can further include an oxidase in a bactericidally effective quantity, such as glucose oxidase, as well as a substrate for the oxidase, such as glucose when the oxidase is glucose oxidase.

Another aspect of the present invention is a method of treating an airway passage infection comprising the step of administering a quantity of a composition according to the present invention to a subject with an airway infection in order to treat the infection. The infection is typically pneumonia and is caused by M. pneumoniae. The method can further comprise administering an antibiotic that is effective in the treatment of M. pneumoniae in a quantity effective to exert a bactericidal action against M. pneumoniae, the antibiotic being administered by a route other than the route of administration of the composition. Alternatively, the composition according to the present invention can include an antibiotic that is effective in the treatment of M. pneumoniae, in which case the method can further comprise the administration of the same antibiotic or a different antibiotic by a different route.

DETAILED DESCRIPTION OF THE INVENTION

Antibiotics are the primary treatment for airway infections but, as discussed earlier, generally only kill free-floating bacteria. It is difficult if not impossible, for antibiotics to kill bacteria embedded in a biofilm.

By the application of a biofilm-dissolving enzyme system first to the airway or together with an antibiotic, the antibiotic is made much more effective.

In general, a biofilm-dissolving enzyme suitable for use in compositions and methods according to the present invention is an enzyme that catalyzes the hydrolysis of a bond that connects two monosaccharides in a polysaccharide or that connects a monosaccharide with a protein molecule in a glycoprotein. These enzymes are referred to herein as "glycoside linkage-hydrolyzing enzymes."

Biofilm-dissolving enzymes suitable for use in compositions and methods according to the present invention include, but are not limited to, xylanase, β-glucanase, cellulase, α-galactosidase, glucanases, amylase, hyaluronidase, polygalacturonase (pectinase), dextranase, and cellobiohydrolase. Other hydrolytic enzymes that are capable of dissolving a bond that connects two monosaccharides in a polysaccharide or that connects a monosaccharide with a protein molecule in a glycoprotein can also be used, including, but not limited to, pullulanase, glycosylceramidase, glucan 1,4-α-glucosidase, oligo-1,6-glucosidase, fucoidanase, glycosylceramidase, thioglucosidase, and glycopeptide N-glycosidase, as well as other enzymes.

Xylanase (EC 3.2.1.8), more precisely, endo-1,4-β-xylanase, is the name given to a class of enzymes that degrade the linear polysaccharide β-1,4-xylan into the monosaccharide xylose. Xylanase catalyzes the endohydrolysis of 1,4-β-D-xylosidic linkages in xylans. Xylanase is produced by many microorganisms, including Thermomyces lanuginosus. Information on xylanase is available at www.brenda.unikoeln.de.

β-glucanase (EC 3.2.1.6), more precisely, endo-1,3(4)-β-glucanase, is an enzyme that catalyzes the endohydrolysis of 1,3- or 1,4-linkages in β-D-glucans when the D-glucose residue whose reducing group is involved in the linkage to be hydrolyzed is itself substituted at C-3. Many sources of β-glucanase are known, particularly from plants and fungi, such as *Candida utilis* and *Saccharomyces cerevisiae*. Information on β-glucanase is available at www.brenda.uni-koeln.de.

Cellulase (EC 3.2.1.4) is an enzyme that catalyzes the endohydrolysis of 1,4-β-D-glucosidic linkages in cellulose, lichenin and cereal β-D-glucans. Sources for cellulase include *Aspergillus niger, Clostridium thermocellum*, and *Cellulomonas fimi*. Information on cellulase is available at www.brenda.uni-koeln.de.

α-galactosidase (EC 3.2.1.22) is an enzyme that catalyzes the hydrolysis of terminal, non-reducing alpha-D-galactose residues in α-D-galactosides, including galactose oligosaccharides, galactomannans and galactohydrolase. Sources of α-galactosidase include *A. niger, E. coli, Glycine max* (soybean), and *Lactobacillus plantarum*. Information on α-galactosidase is available at www.brenda.uni-koeln.de.

Glucanase, or 1,3-β-D-glucosidase (EC 3.2.1.39), is an enzyme that catalyzes the hydrolysis of 1,3-β-D-glucosidic linkages in 1,3-β-D-glucans. Sources of glucanase include *Arabidopsis thaliana, C. thermocellum, Hordeum vulgare*, and *Oryza sativa*. Information on glucanase is available at www.brenda.uni-koeln.de.

Amylase, more precisely α-amylase (EC 3.2.1.1) or β-amylase (EC 3.2.1.2), is a class of enzymes that hydrolyzes amylose, a component of starch. The enzyme α-amylase catalyzes the endohydrolysis of 1,4-α-D-glucosidic linkages in polysaccharides containing three or more 1,4-α-D-glucosidic units. Sources of α-amylase include *A. niger, Aspergillus oryzae, Bacillus licheniformis*, and *Bacillus stearothermophilus*. The enzyme β-amylase catalyzes the hydrolysis of 1,4-β-D-glucosidic linkages in polysaccharides so as to remove successive maltose units from the non-reducing ends of the chains. Sources of β-amylase include *H. vulgare* and *Bacillus cereus*. Information on α-amylase is available at www.brenda.unikoeln.de. Information on β-amylase is available at www.brenda.uni-koeln.de.

Hyaluronidase, more precisely hyaluronate lyase (EC 4.2.2.1), catalyzes the cleavage of hyaluronate chains at a β-D-GalNAc-(1-4)-β-D-GlcA bond, ultimately breaking the polysaccharide down to 3-(4-deoxy-β-D-gluc-4-enuronosyl)-N-acetyl-D-glucosamine. Sources for hyaluronidase include *Candida albicans* and *Streptomyces griseus*. Information on hyaluronidase is available at www.brenda.uni-koeln.de.

Polygalacturonase, also known as pectinase, and whose systematic name is poly(1,4-α-D-galacturonide glycanohydrolase (EC 3.2.1.15), catalyzes the hydrolysis of 1,4-α-D-galactosiduronic linkages in pectate and other galacturonans. Sources for polygalacturonase include *A. niger* and *G. max*. Information on polygalacturonase is available at www.brenda.unikoeln.de. A suitable preparation of pectinase is marketed by Novo Nordisk as Pectinex Ultra SPL™.

Dextranase, whose systematic name is 1,6-α-D-glucan 6-glucanohydrolase, catalyzes the endohydrolysis of 1,6-α-D-glucoside linkages in dextran. Sources of dextranase include *Penicillum funiculosum* and *Avena sativa*. Information on dextranase is available at www.brenda.unikoeln.de.

Cellobiohydrolase, also known as cellulase, and whose systematic name is 1,4-(1,3;1,4)-β-D-glucan 4-glucanohydrolase (EC 3.2.1.4), catalyzes the endohydrolysis of 1,4-β-D-glucosidic linkages in cellulose, lichenin and cereal β-D-glucans. Sources of cellobiohydrolase include *A. niger* and *Clostridium cellulolyticum*. Information on cellobiohydrolase is available at www.brenda.uni-koeln.de.

One or more of these enzymes is included in a composition according to the present invention, together with a pharmaceutically acceptable carrier suitable for administration into an airway passage. Accordingly, one embodiment of the present invention is a composition for removal of biofilm in an airway passage comprising:

(1) a quantity of at least one enzyme that catalyzes the hydrolysis of a bond that connects two monosaccharides in a polysaccharide or that connects a monosaccharide with a protein molecule in a glycoprotein sufficient to break down biofilm in an airway passage; and (2) a pharmaceutically acceptable carrier suitable for administration into the airway passage.

The pharmaceutically acceptable carrier suitable for administration into the airway passage can include buffers, ingredients to control the viscosity of the composition, preservatives, and other conventional ingredients as known in the art. Examples of specific ingredients included in the compositions are provided below in Formulation 1 through Formulation 26.

Various pharmaceutically acceptable carriers known in the art that are suitable for administration into the airway passage can be used in compositions according to the present invention. Typically, in compositions according to the present invention, the pharmaceutically acceptable carrier includes one or more component selected from the group consisting of water, glycerol, and propylene glycol. In one alternative, the carrier comprises water, which is a suitable carrier by itself. In another alternative, the carrier comprises glycerol. In yet another alternative, the carrier comprises water and glycerol. In still another alternative, the carrier comprises water, glycerol, and propylene glycol.

Compositions according to the present invention can further include at least one ingredient in a quantity effective to prevent or inhibit inflammation in the airway. A suitable ingredient is a steroid, such as, but not limited to, a steroid selected from the group consisting of hydrocortisone, beclomethasone, budenoside, ciclesonide, flunisolide, fluticasone, methylprednisolone, prednisolone, prednisone, and triamcinolone, and the salts, solvates, analogues, congeners, bioisosteres, hydrolysis products, metabolites, precursors, and prodrugs thereof. A preferred steroid is hydrocortisone.

Compositions according to the present invention can further include an antibiotic that is effective in the treatment of *M. pneumoniae* in a quantity effective to exert a bactericidal action against *M. pneumoniae*. The antibiotic included in a composition according to the present invention can be, for example, amikacin; a broad-spectrum penicillin such as, but not limited to, ticarcillin, piperacillin, mezlocillin, or azlocillin, ceftazidime, cefepime, ciprofloxacin, tobramycin, aztreonam, imipenem, or meropenem. Alternatively, an antibiotic such as the antibiotics recited above can be administered separately to promote killing of the bacteria in the biofilm. If administered separately, the antibiotic can be administered topically or systemically.

In another alternative, compositions according to the present invention can further include an antiviral agent, such as, but not limited to, an antiviral agent active against one or more strains of the influenza virus. Such antiviral agents include, but are not limited to, amantadine, oseltamivir, rimantadine, zanamivir, and ribavirin. Frequently, in patients with chronic bacterial infections such as those caused by *M. pneumoniae*, infections such as those caused by influenza virus create serious complications such as acute pneumonia or bronchitis; such complications can be life-threatening. Alternatively, the antiviral agent can be administered separately as above.

In still another alternative, compositions according to the present invention can further include an antifungal agent, such as, but not limited to, an antifungal agent active against one or more fungi capable of causing systemic infections affecting the respiratory tract. Such fungi include, but are not limited to *Cryptococcus neoformans, Coccidioides immitis, Histoplasma capsulatum, Blastomyces dermatitidis, Candida* species such as *C. albicans, Aspergillus* species such as *A. fumigatus, Mucor species*, and *Rhizopus* species. Such antifungal agents include, but are not limited to amphotericin B, itraconazole, ketoconazole, fluconazole, flucytosine, clotrimazole, miconazole, econazole, butoconazole, oxiconazole, sulconazole, terconazole, caspofungin acetate, griseofulvin, and terbinafine. Alternatively, the antifungal agent can be administered separately as above.

Compositions according to the present invention can further include a quantity of at least one additional antibacterial enzyme that is selected from the group consisting of lysozyme, lactoferrin, and a peroxidase in a quantity sufficient to exert a bactericidal action. Typically, the peroxidase is selected from the group consisting of lactoperoxidase, myeloperoxidase, horseradish peroxidase, eosinophil peroxidase, and glutathione peroxidase. Preferably, the peroxidase is selected from the group consisting of lactoperoxidase and myeloperoxidase. More preferably, the peroxidase is lactoperoxidase. Lactoperoxidase is a glycoprotein which, in one commercial embodiment, is a lyophilized powder derived from milk. This commercial peroxidase has an activity of 80 IU/mg and a projected molecular weight of 93,000 for L-tyrosine iodination. The physicochemical properties reported for lactoperoxidase include a molecular weight of 78,000, a partial specific volume, reflective of the amino acid composition, of 0.74 and the presence of 1.0 mole of heme per mole of lactoperoxidase. If the antibacterial composition is based on enzymes then a two-part system is preferable. This two-part system comprises:

(1) a first component comprising:
  (a) one of:
    (i) an oxidoreductase enzyme that produces hydrogen peroxide by catalyzing the oxidation of a substrate for which the oxidoreductase enzyme is specific, the first component comprising a sufficient quantity of the oxidoreductase enzyme that a quantity of hydrogen peroxide sufficient to react with a peroxidase is produced; and
    (ii) a substrate that is oxidizable in a reaction catalyzed by the oxidoreductase enzyme in a sufficient quantity, that a quantity of hydrogen peroxide sufficient to react with a peroxidase is produced;
  (b) a peroxidase enzyme that catalyzes a reaction between hydrogen peroxide and a salt that acts as an oxygen acceptor and is capable of reacting with hydrogen peroxide to form a biocide, the peroxidase enzyme being present in a sufficient quantity such that the biocide is produced in a therapeutically effective concentration; and
  (c) an aqueous or nonaqueous medium in which the enzymes and the oxidizable substrate, if present, are stable; and (2) a second component comprising:
  (a) the other of the oxidoreductase enzyme and the substrate that is oxidizable in a reaction catalyzed by the oxidoreductase enzyme that is not present in (1); and
  (b) a salt that acts as an oxygen acceptor and is capable of reacting with hydrogen peroxide to form a biocide in a quantity sufficient to form a therapeutically effective concentration of biocide; and;
  (c) an aqueous or nonaqueous medium in which the other of the oxidoreductase enzyme and the oxidizable substrate and the salt that acts as an oxygen acceptor are stable, with the proviso that one of the media of the first component and the second component is aqueous.

This embodiment is particularly suitable for the treatment of diseases and conditions such as those caused by fungus in which there is no additional endogenous hydrogen peroxide or only a minimal quantity of endogenous hydrogen peroxide produced by the disease process. In this embodiment, therefore, an oxidizable substrate and an oxidoreductase enzyme specific for the substrate is added in order to ensure an adequate amount of hydrogen peroxide to create an effective quantity of biocide.

Typically, the composition comprises from about 0.5 to about 500 International Units of the oxidoreductase enzyme. Typically, the composition comprises from about 0.015 to about 0.6 millimole of the oxidizable substrate. Typically, the composition comprises from about 0.05 to about 30 International Units of the peroxidase enzyme. Typically, the composition comprises from about 0.0001 to about 0.01 millimole of the salt that acts as an oxygen acceptor.

In one alternative, the media of the first and second component are both aqueous media. In another alternative, the medium of the first can be a nonaqueous medium such as glycerol. As used herein, the term "aqueous" does not exclude nonaqueous ingredients such as glycerol or sorbitol, as long as a significant proportion of water is present in the medium.

Ingredients can be interchanged between the first and second components, as shown below in the Examples. For example, the substrate that is oxidizable in a reaction catalyzed by the oxidoreductase enzyme can be included in the first component, and the oxidoreductase enzyme can be included in the second component.

More than one peroxidase enzyme can be included. For example, the first component can comprise both lactoperoxidase and horseradish peroxidase. Other combinations of peroxidases can be used.

The first component and the second component can be prepared separately and mixed before use.

As used herein, the term International Unit (IU) is defined as the quantity of enzyme that catalyzes the conversion of one micromole of substrate per minute under defined standard assay conditions for that enzyme.

If the composition includes a peroxidase enzyme such as lactoperoxidase, myeloperoxidase, horseradish peroxidase, and eosinophil peroxidase, or glutathione peroxidase, the composition can further include at least one substrate that can be converted to an ion with bactericidal properties by the enzymatic action of the peroxidase enzyme. The substrate is present in a quantity such that an effective concentration of the ion with bactericidal properties is produced by the catalytic action of the peroxidase enzyme. Suitable substrates include, but are not limited to, alkali metal salts of anions such as thiocyanate, iodate, or chlorate. The alkali metal salt is typically a sodium or potassium salt, although other alkali metal salts such as lithium or cesium can alternatively be used. The peroxidase enzyme catalyzes the conversion of thiocyanate into hypothiocyanite (—OSCN), molecular oxygen ($O_2$), and water. The peroxidase enzyme similarly catalyzes the conversion of iodate or chlorate to hypoiodite or hypochlorite. These anions possess bactericidal activity.

In an alternative composition according to the present invention that includes a peroxidase, a catalase inhibitor is further included. The effectiveness of the peroxidase enzyme can be affected by the presence of catalase, which is present in many tissues. Catalase competes with peroxidase for hydrogen peroxide. In order to reduce the loss of hydrogen peroxide through the presence of catalase, an effective amount of an enzymatic inhibitor that is specific for catalase can be advantageously incorporated into a composition according to the present invention. Suitable enzymatic inhibitors specific for catalase include, but are not limited to, ascorbic salts such as sodium ascorbate, potassium ascorbate, calcium ascorbate, ascorbyl palmitate, or mixtures thereof, and can be included in a composition according to the invention. An effective concentration of ascorbic salt in compositions according to the present invention is from about $1 \times 10^{-6}$ to about $1 \times 10^{-4}$ millimole per gram of composition. Iron salts such as ferrous sulfate, ferrous chloride, or ferrous iodide can also be incorporated into a composition according to the present invention as a potentiator for the ascorbic salt in its role as catalase inhibitor. A particularly preferred iron salt is ferrous sulfate.

Compositions according to the present invention that include a peroxidase enzyme and the at least one substrate that can be converted to an ion with bactericidal properties by the enzymatic action of the peroxidase enzyme can also advantageously be formulated with an aminohexose in order to increase the yield or accumulation of oxidized anionic biocidal agent, the quantity of the aminohexose being effective to increase the yield or accumulation of oxidized anionic biocidal agent. Typically, the aminohexose is an aminoglucose, but other aminohexoses such as arninogalactose can alternatively be used. Typically, the aminoglucose is selected from the group consisting of glucosamine, N-acetylglucosamine, and mixtures thereof. The aminoglucose is typically present in the composition in a concentration of from about 0.0001 millimole to about 0.002 millimole per gram of composition. Preferably, the aminoglucose is present in the composition in a concentration of from about 0.0003 millimole to about 0.001 millimole per gram of composition.

Compositions according to the present invention that include a peroxidase can further include an oxidase in a bactericidally effective quantity and, optionally, a substrate for the oxidase in a bactericidally effective quantity. The oxidase oxidizes the substrate and produces hydrogen peroxide, which is then used as a substrate by the peroxidase if present. The use of an oxidase is only required if a peroxidase is also present.

The oxidoreductase enzyme is typically selected from the group consisting of glucose oxidase, galactose oxidase, urate oxidase, choline oxidase, D-amino acid oxidase, D-glutamate oxidase, glycine oxidase, glycolic oxidase, L-sorbose oxidase, alcohol oxidase, and amine oxidase. Other enzymes can alternatively be used, such as nitroethane oxidase, D-aspartate oxidase, L-aminoacid oxidase, pyridoxamine phosphate oxidase, ethanolamine oxidase, pyruvate oxidase, oxalate oxidase, hexose oxidase, cholesterol oxidase, aryl alcohol-,oxidase, pyridoxine 4-oxidase, dehydroorotate oxidase, lathosterol oxidase, sarcosine oxidase, N methylaminoacid oxidase, $N^6$-methyllysine oxidase, 6-hydroxy-L-nicotine oxidase, 6-hydroxy-D-nicotine oxidase, 3-hydroxyanthranilate oxidase, aldehyde oxidase, and xanthine oxidase, as described in U.S. Pat. No. 4,340,448 to Schiller et al., incorporated herein by this reference.

For these enzymes, glucose oxidase catalyzes the reaction of β-D-glucose, water, and oxygen to produce hydrogen peroxide and gluconic acid. Galactose oxidase catalyzes the reaction of D-galactose and oxygen to produce hydrogen peroxide and D-galacto-hexodialdose. Urate oxidase catalyzes the reaction of uric acid, water, and oxygen to produce hydrogen peroxide, allantoin, and carbon dioxide. Choline oxidase catalyzes the reaction of choline and oxygen to produce hydrogen peroxide and betaine aldehyde. D-amino acid oxidase catalyzes the reaction of D-amino acids such as D-proline, D-methionine, D-isoleucine, D-alanine, D-valine, or D-phenylalanine with water and oxygen to produce hydrogen peroxide, ammonia, and the α-keto acid corresponding to the D-amino acid being oxidized. D-glutamate oxidase catalyzes the reaction of D-glutamic acid, water, and oxygen to produce hydrogen peroxide, ammonia, and 2-ketoglutarate. Glycine oxidase catalyzes the reaction of glycine, water, and oxygen to produce hydrogen peroxide, ammonia, and glyoxylic acid. Glycolic acid oxidase (also known as 2-hydroxyacid oxidase) catalyzes the reaction of glycolic acid and oxygen to produce 2-ketoacetic acid and hydrogen peroxide. L-sorbose oxidase catalyzes the reaction of L-sorbose and oxygen to produce 5-dehydro-D-fructose and hydrogen peroxide. Alcohol oxidase catalyzes the reaction of a lower primary alcohol or an unsaturated alcohol and oxygen to produce the corresponding aldehyde and hydrogen peroxide. Amine oxidase catalyzes the reaction of an amine, typically a primary amine, but also, in some cases, a secondary or tertiary amine, water, and oxygen to produce the corresponding aldehyde, ammonia, and hydrogen peroxide. In an illustrative reaction, glucose oxidase catalyzes the reaction of β-D-glucose, water, and oxygen during application to the tissues of the airway to produce hydrogen peroxide and gluconic acid.

The properties of a number of preferred oxidases suitable for use in compositions according to the present invention are known. For example, glucose oxidase from *Aspergillus niger* has been determined to have a molecular weight of 150,000 (Pazur et al. (1965)). The enzyme is a glycoprotein containing two molecules of the redox coenzyme flavin adenine dinucleotide (FAD). The amino acid composition has been determined. The isoelectric point of the enzyme is 4.2. The optimum pH of the enzyme is 5.5 with a broad pH range of from 4 to 7. Inhibitors of the enzyme include monovalent silver ions and divalent mercury and copper ions.

Galactose oxidase from *Dactylium dendroides* has a molecular weight of 42,000. It is a metalloenzyme containing one gram-atom of copper per mole. The amino acid composition has been determined. The optimum pH of the enzyme is 7.

Urate oxidase (uricase) from hog liver or beef liver has a molecular weight of 100,000. It is a metalloenzyme containing one gram-atom of copper per mole. The isoelectric point of the enzyme is 6.3. The optimum pH of the enzyme is 9.

D-amino acid oxidase from hog kidney has a molecular weight of 90,000. The enzyme is a glycoprotein containing two molecules of flavin adenine dinucleotide. The optimum pH of the enzyme is 9.1. Certain heavy metals are inhibitors of the enzyme.

The oxidizable substrate is typically present in the composition at a concentration of from about 0.015 millimoles per milliliter of liquid to about 0.6 millimoles per gram of composition. Preferably, the oxidizable substrate is present in the composition at a concentration of from about 0.025 millimoles per gram of composition to about 0.1 millimole per gram of composition. The salt that acts as an oxygen acceptor is typically present in the composition at a concentration of from about 0.0001 millimole to about 0.01 millimole per gram of composition. The salt that acts as an oxygen acceptor is preferably present in the composition at a concentration of from about 0.001 millimole to about 0.006 millimole per gram of composition.

Typically, the oxidoreductase enzyme is present in the composition in a concentration of from about 0.5 IU to about 500 IU per gram of composition. Preferably, the oxidoreductase enzyme is present in the composition in a concentration of from about 10 IU to about 40 I U per gram of composition. Oxidoreductase enzymes are supplied in dry or liquid form with the label specifying the concentration in International Units on a per gram or per milliliter basis, as appropriate.

A particularly preferred oxidase is glucose oxidase. If glucose oxidase is included in a composition according to the present invention, a preferred substrate for the glucose oxidase, to be included in the composition, is β-D-glucose. If another oxidase enzyme is used, appropriate substrates are described above.

In particular, the following combinations of glycoside linkage-hydrolyzing enzymes and peroxidases, if present, can be used in compositions according to the present invention: (1) pectinase as the glycoside linkage-hydrolyzing enzyme; (2) dextranase and pectinase as the glycoside linkage-hydrolyzing enzymes; (3) dextranase and pectinase as the glycoside linkage-hydrolyzing enzymes, plus lactoperoxidase as the peroxidase; (4) pectinase as the glycoside linkage-hydrolyzing enzyme, plus lactoperoxidase as the peroxidase; (5) dextranase and xylanase as the glycoside linkage-hydrolyzing enzymes; (6) α-galactosidase and amylase as the glycoside linkage-hydrolyzing enzymes; (7) pectinase and amylase as the glycoside linkage-hydrolyzing enzymes, plus lactoperoxidase as the peroxidase; (8) dextranase, pectinase, and β-D-glucosidase as the glycoside linkage-hydrolyzing enzymes, plus lactoperoxidase as the peroxidase; (9) dextranase, pectinase, and cellulase as the glycoside linkage-hydrolyzing enzymes, plus lactoperoxidase as the peroxidase; and (10) dextranase, pectinase, cellulase, amylase, and xylanase as the glycoside linkage-hydrolyzing enzymes, plus lactoperoxidase as the peroxidase. Other combinations are possible. These combinations can be combined with lysozyme and/or lactoferrin. Additionally, as indicated above, glucose oxidase or another oxidase can be included as a source of peroxide, plus a substrate for the oxidase such as β-D-glucose.

Other ingredients generally known in the pharmaceutical art can be incorporated into compositions according to the present invention, including colorants, chelating agents, preservatives, and stabilizers, with the proviso that these additional ingredients do not inhibit the hydrolytic and oxidation-reduction reactions on which the activity of the compositions according to the present invention depend.

The composition can further comprise a thickener to provide the composition with an enzyme immobilizing viscosity which inhibits enzymatic action during processing and in packing. A preferred thickener is hydroxypropylcellulose (Klucel). Other thickeners are known in the art and can be alternatively used. These thickeners include hydroxymethyl cellulose, methyl cellulose, polyvinylpyrrolidone (PVP), PVM, PVM/MA copolymers, xanthan gum, and mixtures thereof.

The composition can be aqueous or non-aqueous. If the composition is aqueous, the concentration of water (w/w) typically is from about 0.120% to about 99.993% of water, depending on the exact combination of ingredients included in the composition and the presence or absence of significant proportions of carrier ingredients such as glycerol, propylene glycol, or tripropylene glycol. However, the composition can be a non-aqueous composition with essentially no water content.

In one preferred alternative, the composition is formulated to treat airway infections. As used herein, the terms "treat," "treating," "treatment," and analogous terminology does not imply a cure for airway infections or any other disease or condition; rather, this terminology is used to refer to any clinically detectable improvement in the disease or condition being treated, including, but not limited to, reduction in bacterial numbers or viability, reduction in fever, reduction in pain, reduction in sputum production, reduction in coughing, improvement in a measure of airway functioning, reduction in occurrence of rales or other indicator of airway dysfunction, improvement in subjective well-being experienced by the patient, or any other clinically detectable improvement.

In one preferred alternative, the composition is formulated to treat infection by *Mycoplasma pneumoniae*.

In another preferred alternative, the composition is formulated to treat infection by other bacteria that are responsible for respiratory infections.

In yet another preferred alternative, the composition is formulated to treat viral airway infections, either alone or together with bacterial respiratory infections. The presence of biofilm reduces the resistance of the patient and increases the susceptibility of the patient to secondary infections, which can be either bacterial or viral.

The physical form of a composition according to the present invention can be, for example, a solution.

Compositions according to the present invention can be formulated by techniques known in the art, including techniques that are conventional in the cosmetic art and in the art of over-the-counter and prescription drug composition for blending lipid-soluble components and water-soluble components for the preparation of liquids. These mixing techniques include both manual and mechanical mixing, and include homogenization mixing and sweep mixing. The mixing techniques to be used can be chosen by one of ordinary skill in the art based on variables such as the viscosity of the components to be mixed and the volume of those components, as well as the relative proportion of lipid-soluble and water-soluble ingredients, the proportion of water, and the final physical form of the desired composition.

Particular embodiments of compositions according to the present invention include, but are not limited to, the following:

Formulation 1 is an aqueous composition including the enzyme pectinase. In these formulations, percentages are given in terms of (w/w).

Typically, Formulation 1 comprises:
(1) from about 0.072% to about 0.0108% of pectinase;
(2) optionally, from about 12.33% to about 18.49% of glycerol;
(3) optionally, from about 0.352% to about 0.528% of hydroxypropylcellulose; and
(4) a proportion of water such that the water makes up the remainder of the composition to 100%.

Preferably, Formulation 1 comprises:
(1) from about 0.0072% to about 0.0108% of pectinase; and
(2) from about 99.989% to about 99.993% of water.

More preferably, Formulation 1 comprises:
(1) about 0.009% of pectinase; and
(2) about 99.991% of water.

Formulation 2 is another aqueous formulation including pectinase. Formulation 2 contains hydrocortisone.

Typically, Formulation 2 comprises:
(1) from about 52.761% to about 64.485% of propylene glycol;
(2) optionally, from about 3.0% to about 15.0% of glycerol;
(3) from about 0.80% to about 1.20% of hydrocortisone;
(4) from about 0.08% to about 0.12% of pectinase; and
(5) a proportion of water such that the water makes up the remainder of the composition to 100%.

Preferably, Formulation 2 comprises:
(1) from about 52.761% to about 64.485% of propylene glycol;
(2) from about 36.770% to about 44.942% of water;
(3) from about 0.80% to about 1.20% of hydrocortisone; and
(4) from about 0.08% to about 0.12% of pectinase.

More preferably, Formulation 2 comprises:
(1) about 58.623% of propylene glycol;
(2) about 40.856% of water;
(3) about 1.00% of hydrocortisone; and
(4) about 0.010% of pectinase.

Formulation 3 is an aqueous composition including the two enzymes dextranase and pectinase.

Typically, Formulation 3 comprises:
(1) from about 0.08% to about 0.12% of dextranase;
(2) from about 0.08% to about 0.12% of pectinase;
(3) from about 1.152% to about 1.728% of tripropylene glycol;
(4) from about 2.405% to about 3.607% of benzyl alcohol;
(5) optionally, from about 5.00% to about 15.00% of glycerol;
(6) optionally, from about 10.00% to about 30.00% of propyleneglycol; and
(7) a proportion of water such that the water makes up the remainder of the composition to 100%.

Preferably, Formulation 3 comprises:
(1) from about 0.08% to about 0.12% of dextranase;
(2) from about 0.08% to about 0.12% of pectinase;
(3) from about 1.152% to about 1.728% of tripropylene glycol;
(4) from about 2.405% to about 3.607% of benzyl alcohol; and
(5) from about 94.425% to about 96.283% of water.

More preferably, Formulation 3 comprises:
(1) about 0.010% of dextranase; and
(2) about 0.010% of pectinase
(3) about 1.440% of tripropylene glycol;
(4) about 3.006% of benzyl alcohol; and
(5) about 95.033% of water.

Formulation 4 is an aqueous composition including dextranase.

Typically, Formulation 4 comprises:
(1) from about 2.405% to about 3.607% of benzyl alcohol;
(2) from about 0.008% to about 0.012% of dextranase;
(3) optionally, from about 5.00% to about 15.00% of glycerol;
(4) optionally, from about 10.00% to about 30.00% of propylene
(5) optionally, from about 0.40% to about 0.60% of hydroxypropylcellulose; and
(6) a proportion of water such that the water makes up the remainder of the composition to 100%.

Preferably, Formulation 4 comprises:
(1) from about 2.405% to about 3.607% of benzyl alcohol;
(2) from about 0.008% to about 0.012% of dextranase; and
(3) from about 96.381% to about 97.587% of water.

More preferably, Formulation 4 comprises:
(1) about 3.006% of benzyl alcohol;
(2) about 0.10% of dextranase; and
(3) about 96.984% of water.

Formulation 5 is an aqueous composition including dextranase and pectinase, and further including lactoperoxidase as a source of hydrogen peroxide. Formulation 5 optionally further includes hydroxypropylcellulose.

Typically, Formulation 5 comprises:
(1) from about 16.328% to about 24.492% of glycerol;
(2) from about 63.561% to about 76.490% of propylene glycol;
(3) optionally, from about 0.40% to about 0.60% of hydroxypropylcellulose;
(4) from about 2.405% to about 3.607% of benzyl alcohol;
(5) from about 0.008% to about 0.012% of dextranase;
(6) from about 0.008% to about 0.012% of lactoperoxidase;
(7) from about 0.008% to about 0.012% of pectinase; and
(8) from about 4.353% to about 6.529% of water.

Preferably, Formulation 5 comprises:
(1) about 20.410% of glycerol;
(2) about 70.623% of propylene glycol;
(3) about 3.006% of benzyl alcohol;
(4) about 0.010% of dextranase;
(5) about 0.010% of lactoperoxidase;
(6) about 0.020% of pectinase; and
(7) about 5.941% of water.

Formulation 6 is an aqueous composition including dextranase and pectinase, and further including lysozyme and lactoferrin. Formulation 6 further includes hydroxypropylcellulose.

Typically, Formulation 6 comprises:
(1) from about 88.784% to about 92.522% of glycerol;
(2) from about 0.40% to about 0.60% of hydroxypropylcellulose;
(3) from about 2.405% to about 3.607% of benzyl alcohol;
(4) from about 0.08% to about 0.12% of lysozyme;
(5) from about 0.08% to about 0.12% of lactoferrin;
(6) from about 0.08% to about 0.12% of lactoperoxidase;
(7) from about 0.08% to about 0.12% of pectinase; and
(8) from about 4.353% to about 6.529% of water.

Preferably, Formulation 6 comprises:
(1) about 90.933% of glycerol;
(2) about 0.50% of hydroxypropylcellulose;
(3) about 3.006% of benzyl alcohol;
(4) about 0.010% of lysozyme;
(5) about 0.010% of lactoferrin;
(6) about 0.010% of lactoperoxidase;
(7) about 0.010% of pectinase; and
(8) about 5.441% of water.

Formulation 7 is an aqueous composition including dextranase, lactoperoxidase, and pectinase. Formulation 7 omits benzyl alcohol.

Typically, Formulation 7 comprises:
(1) from about 16.830% to about 25.246% of glycerol;
(2) from about 0.412% to about 0.618% of hydroxypropylcellulose;
(3) from about 0.00824% to about 0.0124% of dextranase;
(4) from about 0.00824% to about 0.0124% of lactoperoxidase;
(5) from about 0.00824% to about 0.0124% of pectinase; and
(6) from about 70.004% to about 84.978% water.

Preferably, Formulation 7 comprises:
(1) about 21.038% of glycerol;
(2) about 0.515% of hydroxypropylcellulose;
(3) about 0.0103% of dextranase;
(4) about 0.0103% of lactoperoxidase;

(5) about 0.0103% of pectinase; and
(6) about 78.416% of water.

Formulation 8 is an aqueous composition including dextranase, lactoperoxidase, and pectinase and that includes glycerol, propylene glycol, and tripropylene glycol. Formulation 8 omits benzyl alcohol.

Typically, Formulation 8 comprises:
(1) from about 25.201% to about 37.813% of glycerol;
(2) from about 47.114% to about 57.584% of propylene glycol;
(3) from about 8.375% to about 12,563% of tripropylene glycol;
(4) from about 0.00832% to about 0.0125% of dextranase;
(5) from about 0.00832% to about 0.0125% of lactoperoxidase;
(6) from about 0.00832% to about 0.0125% of pectinase; and
(7) from about 4.510% to about 6.766% of water.

Preferably, Formulation 8 comprises:
(1) about 31.511% of glycerol;
(2) about 52.349% of propylene glycol;
(3) about 10.469% of tripropylene glycol;
(4) about 0.0104% of dextranase;
(5) about 0.0104% of lactoperoxidase;
(6) about 0.0104% of pectinase; and
(7) about 5.638% of water.

Formulation 9 is an aqueous composition including dextranase and xylanase and that includes glycerol and tripropylene glycol. Formulation 9 omits benzyl alcohol.

Typically, Formulation 9 comprises:
(1) from about 16.919% to about 25.379% of glycerol;
(2) from about 56.440% to about 68.982% of propylene glycol;
(3) from about 8.383% to about 12.575% of tripropylene glycol;
(4) from about 0.00832% to about 0.0125% of dextranase;
(5) from about 0.00832% to about 0.0125% of xylanase; and
(6) from about 4.510% to about 6.766% of water.

Preferably, Formulation 9 comprises:
(1) about 21.149% of glycerol;
(2) about 62.711% of propylene glycol;
(3) about 10.479% of tripropylene glycol;
(4) about 0.104% of dextranase;
(5) about 0.104% of xylanase; and
(6) about 5.638% of water.

Formulation 10 is similar to Formulation 9, but omits propylene glycol and replaces the proportion of propylene glycol in Formulation 9 with tripropylene glycol.

Typically, Formulation 10 comprises:
(1) from about 16.919% to about 25.379% of glycerol;
(2) from about 64.823% to about 78.554% of tripropylene glycol;
(3) from about 0.00832% to about 0.0125% of dextranase;
(4) from about 0.00832% to about 0.0125% of xylanase; and
(5) from about 4.510% to about 6.766% of water.

Preferably, Formulation 10 comprises:
(1) about 21.149% of glycerol;
(2) about 73.190% of tripropylene glycol;
(3) about 0.104% of dextranase;
(4) about 0.104% of xylanase; and
(5) about 5.638% of water.

Formulation 11 is an aqueous composition including α-galactosidase and amylase and that includes glycerol and propylene glycol. Formulation 11 omits benzyl alcohol.

Typically, Formulation 11 comprises:
(1) from about 73.051% to about 84.927% of propylene glycol;
(2) from about 0.460% to about 0.690% of hydroxypropylcellulose;
(3) from about 0.0092% to about 0.0138% of α-galactosidase;
(4) from about 0.0092% to about 0.0138% of amylase; and
(5) from about 14.595% to about 21.893% of water.

Preferably, Formulation 11 comprises:
(1) about 78.989% of propylene glycol;
(2) about 0.575% of hydroxypropylcellulose;
(3) about 0.115% of α-galactosidase;
(4) about 0.115% of amylase; and
(5) about 83.977% of water.

Formulation 12 is an aqueous composition including lactoperoxidase, pectinase, and amylase and that includes glycerol and propylene glycol. Formulation 12 omits benzyl alcohol.

Typically, Formulation 12 comprises:
(1) from about 14.596% to about 21.894% of glycerol;
(2) from about 69.818% to about 82.069% of propylene glycol;
(3) from about 0.00944% to about 0.0141% of lactoperoxidase;
(4) from about 0.0474% to about 0.0710% of pectinase;
(5) from about 0.0190% to about 0.0284% of amylase; and
(6) from about 3.259% to about 4.889% of water.

Preferably, Formulation 12 comprises:
(1) about 18.245% of glycerol;
(2) about 77.576% of propylene glycol;
(3) about 0.0118% of lactoperoxidase;
(4) about 0.0592% of pectinase;
(5) about 0.0237% of amylase; and
(6) about 4.074% of water.

Formulation 13 is an aqueous composition including dextranase, lactoperoxidase, and pectinase. Formulation 13 includes glycerol, propylene glycol, and tripropylene glycol. Formulation 13 further includes potassium thiocyanate. Formulation 13 omits benzyl alcohol.

Typically, Formulation 13 comprises:
(1) from about 25.204% to about 37.806% of glycerol;
(2) from about 47.105% to about 57.572% of propylene glycol;
(3) from about 8.374% to about 12.560% of tripropylene glycol;
(4) from about 0.00832% to about 0.0725% of dextranase;
(5) from about 0.0166% to about 0.0248% of lactoperoxidase;
(6) from about 0.00832% to about 0.0125% of pectinase;
(7) from about 0.00832% to about 0.0125% of potassium thiocyanate; and
(8) from about 4.510% to about 6.764% of water.

Preferably, Formulation 13 comprises:
(1) about 31.505% of glycerol;
(2) about 52.339% of propylene glycol;
(3) about 10.467% of tripropylene glycol;
(4) about 0.0104% of dextranase;
(5) about 0.0207% of lactoperoxidase;
(6) about 0.0104% of pectinase;
(7) about 0.0104% of potassium thiocyanate; and
(8) about 5.637% of water.

Formulation 14 is a non-aqueous composition including dextranase and lactoperoxidase. Formulation 14 includes glycerol and propylene glycol. Formulation 14 further includes potassium thiocyanate. Formulation 14 omits benzyl alcohol.

Typically, Formulation 14 comprises:
(1) from about 12.846% to about 19.268% of glycerol;
(2) from about 75.530% to about 87.112% of propylene glycol;
(3) from about 0.00832% to about 0.0125% of dextranase;
(4) from about 0.0166% to about 0.0250% of lactoperoxidase;
(5) from about 0.00832% to about 0.0125% of pectinase; and
(6) from about 0.00832% to about 0.0125% of potassium
Preferably, Formulation 14 comprises:
(1) about 16.057% of glycerol;
(2) about 83.901% of propylene glycol;
(3) about 0.0104% of dextranase;
(4) about 0.0208% of lactoperoxidase;
(5) about 0.0104% of pectinase; and
(6) about 0.0104% of potassium thiocyanate.

Formulation 15 is a non-aqueous formulation including dextranase, lactoperoxidase, and pectinase. Formulation 15 also includes lysozyme and potassium iodate. Formulation 15 includes glycerol and propylene glycol; it omits benzyl alcohol.

Typically, Formulation 15 comprises:
(1) from about 12.834% to about 19.250% of glycerol;
(2) from about 75.439% to about 87.100% of propylene glycol;
(3) from about 0.00832% to about 0.0125% of dextranase;
(4) from about 0.0166% to about 0.0250% of lactoperoxidase;
(5) from about 0.0166% to about 0.0250% of pectinase;
(6) from about 0.0166% to about 0.0250% of lysozyme; and
(7) from about 0.00832% to about 0.0125% of potassium iodate.

Preferably, Formulation 15 comprises:
(1) about 16.042% of glycerol;
(2) about 83.821% of propylene glycol;
(3) about 0.0104% of dextranase;
(4) about 0.0208% of lactoperoxidase;
(5) about 0.0208% of pectinase;
(6) about 0.0208% of lysozyme; and
(7) about 0.0104% of potassium iodate.

Formulation 16 is a non-aqueous composition including dextranase, lactoperoxidase, and pectinase. Formulation 16 includes glycerol, propylene glycol, and tripropylene glycol, as well as lysozyme, lactoferrin, and potassium iodate. Formulation 16 omits benzyl alcohol.

Typically, Formulation 16 comprises:
(1) from about 8.670% to about 13.004% of glycerol;
(2) from about 75.439% to about 87.091% of propylene glycol;
(3) from about 4.164% to about 6.246% of tripropylene glycol;
(4) from about 0.00832% to about 0.0125% of dextranase;
(5) from about 0.0166% to about 0.0250% of lactoperoxidase;
(6) from about 0.0166% to about 0.0250% of pectinase;
(7) from about 0.0166% to about 0.0250% of lysozyme;
(8) from about 0.00832% to about 0.0125% of lactoferrin; and
(9) from about 0.00832% to about 0.0125% of potassium iodate.

Preferably, Formulation 16 comprises:
(1) about 10.847% of glycerol;
(2) about 83.821% of propylene glycol;
(3) about 5.205% of tripropylene glycol;
(4) about 0.0104% of dextranase;
(5) about 0.0208% of lactoperoxidase;
(6) about 0.0208% of pectinase;
(7) about 0.0208% of lysozyme;
(8) about 0.0104% of lactoferrin; and
(9) about 0.0104% of potassium iodate.

Formulation 17 is a non-aqueous composition including dextranase, lactoperoxidase, pectinase, and β-D-glucosidase. Formulation 17 further includes potassium iodate, as well as glycerol, propylene glycol, and tripropylene glycol. Formulation 17 omits benzyl alcohol.

Typically, Formulation 17 comprises:
(1) from about 8.678% to about 13.016% of glycerol;
(2) from about 75.512% to about 87.104% of propylene glycol;
(3) from about 4.168% to about 6.252% of tripropylene glycol;
(4) from about 0.00832% to about 0.0125% of dextranase;
(5) from about 0.0166% to about 0.0250% of lactoperoxidase;
(6) from about 0.00832% to about 0.0125% of pectinase;
(7) from about 0.00832% to about 0.0125% of β-D-glucosidase;
(8) from about 0.00832% to about 0.0125% of potassium iodate.

Preferably, Formulation 17 comprises:
(1) about 10.847% of glycerol;
(2) about 83.902% of propylene glycol;
(3) about 5.210% of tripropylene glycol;
(4) about 0.0104% of dextranase;
(5) about 0.0208% of lactoperoxidase;
(6) about 0.0104% of pectinase;
(7) about 0.0104% of β-D-glucosidase; and
(8) about 0.0104% of potassium iodate.

Formulation 18 is a non-aqueous formulation that includes dextranase, lactoperoxidase, pectinase, and cellulase. Formulation 18 includes glycerol, propylene glycol, and tripropylene glycol. Formulation 18 further includes potassium thiocyanate. Formulation 18 omits benzyl alcohol.

Typically, Formulation 18 comprises:
(1) from about 17.014% to about 25.520% of glycerol;
(2) from about 66.134% to about 78.768% of propylene glycol;
(3) from about 4.168% to about 6.252% of tripropylene glycol;
(4) from about 0.00832% to about 0.0125% of dextranase;
(5) from about 0.0166% to about 0.0250% of lactoperoxidase;
(6) from about 0.00832% to about 0.0125% of pectinase;
(7) from about 0.00832% to about 0.0125% of cellulase; and
(8) from about 0.00832% to about 0.0125% of potassium thiocyanate.

Preferably, Formulation 18 comprises:
(1) about 21.267% of glycerol;
(2) about 73.482% of propylene glycol;
(3) about 5.210% of tripropylene glycol;
(4) about 0.0104% of dextranase;
(5) about 0.0208% of lactoperoxidase;
(6) about 0.0104% of pectinase;
(7) about 0.0104% of cellulase; and
(8) about 0.0104% of potassium thiocyanate.

Formulation 19 is a non-aqueous composition including dextranase, lactoperoxidase, pectinase, cellulase, amylase, and xylanase, as well as potassium thiocyanate. Formulation 19 includes glycerol, propylene glycol, and tripropylene glycol. Formulation 19 omits benzyl alcohol.

Typically, Formulation 19 comprises:
(1) from about 16.998% to about 25.496% of glycerol;
(2) from about 66.070% to about 78.763% of propylene glycol;
(3) from about 4.164% to about 6.246% of tripropylene glycol;
(4) from about 0.00832% to about 0.0125% of dextranase;
(5) from about 0.0166% to about 0.0250% of lactoperoxidase;
(6) from about 0.00832% to about 0.0125% of pectinase;
(7) from about 0.00832% to about 0.0125% of cellulase;
(8) from about 0.0166% to about 0.0250% of amylase;
(9) from about 0.00832% to about 0.0125% of xylanase; and
(10) from about 0.00832% to about 0.0125% of potassium thiocyanate.

Preferably, Formulation 19 comprises:
(1) about 21.247% of glycerol;
(2) about 73.411% of propylene glycol;
(3) about 5.205% of tripropylene glycol;
(4) about 0.0104% of dextranase;
(5) about 0.0208% of lactoperoxidase;
(6) about 0.0104% of pectinase;
(7) about 0.0104% of cellulase;
(8) about 0.0208% of amylase;
(9) about 0.0104% of xylanase; and
(10) about 0.0104% of potassium thiocyanate.

Formulation 20 is a non-aqueous composition including dextranase, lactoperoxidase, glucose oxidase, pectinase, cellulase, amylase, and xylanase, as well as potassium iodate. Formulation 20 includes glycerol and propylene glycol. Formulation 20 also includes $\beta$-D-glucose. Formulation 20 includes benzyl alcohol.

Typically, Formulation 20 comprises:
(1) from about 19.311% to about 28.967% of glycerol;
(2) from about 65.497% to about 78.212% of propylene glycol;
(3) from about 2.194% to about 3.296% of benzyl alcohol;
(4) from about 0.220% to about 0.330% of $\beta$-D-glucose;
(5) from about 0.00731% to about 0.0110% of dextranase;
(6) from about 0.00658% to about 0.00988% of lactoperoxidase;
(7) from about 0.00585% to about 0.00877% of glucose oxidase;
(8) from about 0.00658% to about 0.00988% of pectinase;
(9) from about 0.00731% to about 0.0110% of dextranase;
(10) from about 0.0146% to about 0.0220% of amylase;
(11) from about 0.00731% to about 0.0110% of xylanase; and
(12) from about 0.00731% to about 0.0110% of potassium iodate.

Preferably, Formulation 20 comprises:
(1) about 24.139% of glycerol;
(2) about 72.775% of propylene glycol;
(3) about 2.747% of benzyl alcohol;
(4) about 0.275% of $\beta$-D-glucose;
(5) about 0.00914% of dextranase;
(6) about 0.00823% of lactoperoxidase;
(7) about 0.00731% of glucose oxidase;
(8) about 0.00823% of pectinase;
(9) about 0.00914% of cellulase;
(10) about 0.0183% of amylase;
(11) about 0.00914% of xylanase; and
(12) about 0.00914% of potassium iodate.

Formulation 21 is a non-aqueous composition including dextranase, lactoperoxidase, glucose oxidase, and pectinase. Formulation 21 includes glycerol and propylene glycol. Formulation 21 further includes hydrocortisone and potassium iodate. Formulation 21 also further includes benzyl alcohol.

Typically, Formulation 21 comprises:
(1) from about 19.142% to about 28.712% of glycerol;
(2) from about 64.924% to about 77.702% of propylene glycol;
(3) from about 2.178% to about 3.268% of benzyl alcohol;
(4) from about 0.725% to about 1.087% of hydrocortisone;
(5) from about 0.218% to about 0.328% of $\beta$-D-glucose;
(6) from about 0.00725% to about 0.0109% of dextranase;
(7) from about 0.00652% to about 0.00978% of lactoperoxidase;
(8) from about 0.00580% to about 0.00870% of glucose oxidase;
(9) from about 0.00725% to about 0.0109% of pectinase; and
(10) from about 0.00725% to about 0.0109% of potassium iodate.

Preferably, Formulation 21 comprises:
(1) about 23.927% of glycerol;
(2) about 72.138% of propylene glycol;
(3) about 2.723% of benzyl alcohol;
(4) about 0.906% of hydrocortisone;
(5) about 0.273% of $\beta$-D-glucose;
(6) about 0.00906% of dextranase;
(7) about 0.00815% of lactoperoxidase;
(8) about 0.00725% of glucose oxidase;
(9) about 0.00906% of pectinase; and
(10) about 0.00906% of potassium iodate.

Formulation 22 is an aqueous composition containing a minimal amount of water. Formulation 22 includes lactoperoxidase, glucose oxidase, and pectinase, and $\beta$-D-glucose. Formulation 22 includes glycerol and propylene glycol, as well as hydroxypropylcellulose. Formulation 22 further includes hydrocortisone and benzyl alcohol, as well as lactoferrin and lysozyme.

Typically, Formulation 22 comprises:
(1) from about 28.328% to about 42.492% of glycerol;
(2) from about 52.761% to about 64.485% of propylene glycol;
(3) from about 1.152% to about 1.728% of hydroxypropylcellulose;
(4) from about 2.405% to about 3.607% of benzyl alcohol;
(5) from about 0.120% to about 0.180% of water;
(6) from about 0.800% to about 1.200% of hydrocortisone;
(7) from about 0.241% to about 0.361% of $\beta$-D-glucose;
(8) from about 0.0064% to about 0.0096% of lactoperoxidase;
(9) from about 0.0008% to about 0.0012% of glucose oxidase; (10) from about 0.0064% to about 0.0096% of lactoferrin; (11) from about 0.0064% to about 0.0096% of lysozyme; (12) from about 0.0080% to about 0.0120% of pectinase; and (13) from about 0.028% to about 0.042% of potassium iodate.

Preferably, Formulation 22 comprises:
(1) about 35.410% of glycerol;
(2) about 58.623% of propylene glycol;
(3) about 1.440% of hydroxypropylcellulose;
(4) about 3.006% of benzyl alcohol;
(5) about 0.150% of water;
(6) about 1.000% of hydrocortisone;
(7) about 0.301% of $\beta$-D-glucose;
(8) about 0.008% of lactoperoxidase;
(9) about 0.001% of glucose oxidase;
(10) about 0.008% of lactoferrin;
(11) about 0.008% of lysozyme;

(12) about 0.010% of pectinase; and
(13) about 0.035% of potassium iodate.

Formulation 23 is the same as Formulation 22 except that it substitutes potassium thiocyanate in Formulation 23 for potassium iodate in Formulation 22.

Typically, Formulation 23 comprises:
(1) from about 28.328% to about 42.492% of glycerol;
(2) from about 52.761% to about 64.485% of propylene glycol;
(3) from about 1.152% to about 1.728% of hydroxypropylcellulose;
(4) from about 2.405% to about 3.607% of benzyl alcohol;
(5) from about 0.120% to about 0.180% of water;
(6) from about 0.800% to about 1.200% of hydrocortisone;
(7) from about 0.241% to about 0.361% of β-D-glucose;
(8) from about 0.0064% to about 0.0096% of lactoperoxidase;
(9) from about 0.0008% to about 0.0012% of glucose oxidase;
(10) from about 0.0064% to about 0.0096% of lactoferrin;
(11) from about 0.0064% to about 0.0096% of lysozyme;
(12) from about 0.0080% to about 0.0120% of pectinase; and
(13) from about 0.028% to about 0.042% of potassium thiocyanate.

Preferably, Formulation 23 comprises:
(1) about 35.410% of glycerol;
(2) about 58.623% of propylene glycol;
(3) about 1.440% of hydroxypropylcellulose;
(4) about 3.006% of benzyl alcohol;
(5) about 0.150% of water;
(6) about 1.000% of hydrocortisone;
(7) about 0.301% of β-D-glucose;
(8) about 0.008% of lactoperoxidase;
(9) about 0.001% of glucose oxidase;
(10) about 0.008% of lactoferrin;
(11) about 0.008% of lysozyme;
(12) about 0.010% of pectinase; and
(13) about 0.035% of potassium thiocyanate.

Formulation 24 is similar to Formulation 23, except that it omits hydroxypropylcellulose and benzyl alcohol. Formulation 24 includes potassium thiocyanate.

Typically, Formulation 24 comprises:
(1) from about 31.885% to about 47.827% of glycerol;
(2) from about 52.761% to about 64.485% of propylene glycol;
(3) from about 0.120% to about 0.180% of water;
(4) from about 0.800% to about 1.200% of hydrocortisone;
(5) from about 0.241% to about 0.361% of β-D-glucose;
(6) from about 0.0064% to about 0.0096% of lactoperoxidase;
(7) from about 0.0008% to about 0.0012% of glucose oxidase;
(8) from about 0.0064% to about 0.0096% of lactoferrin;
(9) from about 0.0064% to about 0.0096% of lysozyme;
(10) from about 0.0080% to about 0.0120% of pectinase; and
(11) from about 0.028% to about 0.042% of potassium thiocyanate.

Preferably, Formulation 24 comprises:
(1) about 39.856% of glycerol;
(2) about 58.623% of propylene glycol;
(3) about 0.150% of water;
(4) about 1.000% of hydrocortisone;
(5) about 0.301% of β-D-glucose;
(6) about 0.008% of lactoperoxidase;
(7) about 0.001% of glucose oxidase;
(8) about 0.008% of lactoferrin;
(9) about 0.008% of lysozyme;
(10) about 0.010% of pectinase; and
(11) about 0.035% of potassium thiocyanate.

Formulation 25 is also similar to Formulations 23 and 24, but includes the benzyl alcohol while omitting the hydroxypropylcellulose.

Typically, Formulation 25 comprises:
(1) from about 29.480% to about 44.220% of glycerol;
(2) from about 52.761% to about 64.485% of propylene glycol;
(3) from about 2.405% to about 3.607% of benzyl alcohol;
(4) from about 0.120% to about 0.180% of water;
(5) from about 0.800% to about 1.200% of hydrocortisone;
(6) from about 0.241% to about 0.361% of β-D-glucose;
(7) from about 0.0064% to about 0.0096% of lactoperoxidase;
(8) from about 0.0008% to about 0.0012% of glucose oxidase;
(9) from about 0.0064% to about 0.0096% of lactoferrin;
(10) from about 0.0064% to about 0.0096% of lysozyme;
(11) from about 0.0080% to about 0.0120% of pectinase; and
(12) from about 0.028% to about 0.042% of potassium thiocyanate.

Preferably, Formulation 25 comprises:
(1) about 36.850% of glycerol;
(2) about 58.623% of propylene glycol;
(3) about 3.006% of benzyl alcohol;
(4) about 0.150% of water;
(5) about 1.000% of hydrocortisone;
(6) about 0.301% of β-D-glucose;
(7) about 0.008% of lactoperoxidase;
(8) about 0.001% of glucose oxidase;
(9) about 0.008% of lactoferrin;
(10) about 0.008% of lysozyme;
(11) about 0.010% of pectinase; and
(12) about 0.035% of potassium thiocyanate.

Formulation 26 is an aqueous composition with a minimal amount of water that includes lactoperoxidase, glucose oxidase, pectinase, and dextranase. Formulation 26 includes glycerol and propylene glycol, as well as hydroxypropylcellulose. Formulation 26 further includes lactoferrin and lysozyme, as well as β-D-glucose and potassium thiocyanate. Formulation 26 further includes benzyl alcohol.

Typically, Formulation 26 comprises:
(1) from about 28.328% to about 42.492% of glycerol;
(2) from about 53.652% to about 65.574% of propylene glycol;
(3) from about 1.152% to about 1.728% of hydroxypropylcellulose;
(4) from about 2.405% to about 3.607% of benzyl alcohol;
(5) from about 0.120% to about 0.180% of water;
(6) from about 0.241% to about 0.361% of β-D-glucose;
(7) from about 0.0064% to about 0.0096% of lactoperoxidase;
(8) from about 0.0008% to about 0.0012% of glucose oxidase;
(9) from about 0.0064% to about 0.0096% of lactoferrin;
(10) from about 0.0064% to about 0.0096% of lysozyme;
(11) from about 0.0080% to about 0.0120% of pectinase;
(12) from about 0.0080% to about 0.0120% of dextranase; and
(13) from about 0.028% to about 0.042% of potassium thiocyanate.

Preferably, Formulation 26 comprises:
(1) about 35.410% of glycerol;
(2) about 59.613% of propylene glycol;
(3) about 1.440% of hydroxypropylcellulose;
(4) about 3.006% of benzyl alcohol;
(5) about 0.150% of water;
(6) about 0.301% of β-D-glucose;
(7) about 0.008% of lactoperoxidase;
(8) about 0.001% of glucose oxidase;
(9) about 0.008% of lactoferrin;
(10) about 0.008% of lysozyme;
(11) about 0.010% of pectinase;
(12) about 0.010% of dextranase; and
(13) about 0.035% of potassium thiocyanate.

In another alternative, a composition according to the present invention can further include an antibiotic that is effective is effective in the treatment of *Mycoplasma pneumoniae* in a quantity effective to exert a bacterial action against *M. pneumoniae*. These antibiotics are described above and include, but are not limited to, amikacin; a broad-spectrum penicillin such as, but not limited to, ticarcillin, piperacillin, mezlocillin, or azlocillin; ceftazidime; cefepime; ciprofioxacin; tobramycin; aztreonam; imipenem; or meropenem. Other antibiotics can be used that are effective against other bacteria that can cause airway infections.

Other formulations can be prepared that are similar to the ones described in detail above.

Another embodiment of the present invention is a method of treating an airway infection comprising the step of administering a quantity of a composition according to the present invention as described above to a subject with an airway infection in order to treat the infection. The precise therapeutically effective amount for a subject will depend upon the subject's age, size, weight, and health, the extent of the infection, the bacterium or other microorganism causing the infection, the presence of other conditions such as allergic reactions that can complicate the infection, the route and frequency of administration of the composition according to the present invention, and the therapeutics or combination of therapeutics selected for administration, as well as variables such as liver and kidney function that affect the pharmacokinetics of administered therapeutics. Thus, it is not useful to specify an exact effective amount in advance. However, the effective amount for a given situation can be determined by routine experimentation and is within the judgment of the clinician. The route and frequency of administration, as well, can be determined by one of ordinary skill in the art with reference to the above parameters.

One route of administration that is frequently desirable in treatment of airway infections or other conditions involving the respiratory tract is the use of aerosols. The preparation of compositions for administration as aerosols is described in detail below.

Compositions according to the present invention can be formulated for administration in conjunction with one or more pharmaceutical excipients, depending on the physical form of the composition and the intended route of administration. The pharmaceutical excipients can include, but are not necessarily limited to, calcium carbonate, calcium phosphate, various sugars or types of starch, cellulose derivatives, gelatin, vegetable oils, polyethylene glycols and physiologically compatible solvents. Other pharmaceutical excipients are well known in the art. Similarly, compositions according to the present invention can be formulated for administration in conjunction with one or more pharmaceutically acceptable carriers, again depending on the physical form of the composition and the intended route of administration. Exemplary pharmaceutically acceptable carriers include, but are not limited to, any and/or all of solvents, including aqueous and non-aqueous solvents, dispersion media, coatings, antibacterial and/or antifungal agents, isotonic and/or absorption delaying agent, and/or the like. The use of such media and/or agents for pharmaceutically active substances is well known in the art. Except insofar as any conventional medium, carrier, or agent is incompatible with the active ingredient or ingredients, its use in a composition according to the present invention is contemplated. Supplementary active ingredients can also be incorporated into the compositions, particularly as described above. For compositions according to the present invention, preparations should meet sterility, pyrogenicity, general safety, and purity standards as required by the FDA Office of Biologics Standards or by other regulatory organizations regulating drugs.

Thus, compositions according to the present invention can be formulated for oral, sustained-release oral, buccal, sublingual, inhalation, insufflation, or parenteral administration.

If the composition is administered orally, either in a conventional or a sustained-release preparation, it is typically administered in a conventional unit dosage form such as a tablet, a capsule, a pill, a troche, a wafer, a powder, or a liquid such as a solution, a suspension, a tincture, or a syrup. Oral formulations typically include such normally employed excipients as, for example, pharmaceutical grades of mannitol, lactose, starch, magnesium stearate, sodium saccharin, cellulose, magnesium carbonate, and other conventional pharmaceutical excipients. In certain defined embodiments, oral pharmaceutical compositions will comprise an inert diluent and/or assimilable edible carrier, and/or they may be enclosed in hard or soft shell gelatin capsules. Alternatively, they may be compressed into tablets. As another alternative, particularly for veterinary practice, they can be incorporated directly into food. For oral therapeutic administration, they can be incorporated with excipients or used in the form of ingestible tablets, buccal tablets, dragees, pills, troches, capsules, wafers, or other conventional dosage forms.

The tablets, pills, troches, capsules, wafers, or other conventional dosage forms can also contain the following: a binder, such as gum tragacanth, acacia, cornstarch, sorbitol, mucilage of starch, polyvinylpyrrolidone, or gelatin; excipients or fillers such as dicalcium phosphate, lactose, microcrystalline cellulose, or sugar; a disintegrating agent such as potato starch, croscarmellose sodium, or sodium starch glycolate, or alginic acid; a lubricant such as magnesium stearate, stearic acid, talc, polyethylene glycol, or silica; a sweetening agent, such as sucrose, lactose, or saccharin; a wetting agent such as sodium lauryl sulfate; or a flavoring agent, such as peppermint, oil of wintergreen, orange flavoring, or cherry flavoring. When the dosage unit form is a capsule, it can contain, in addition to materials of the above types, a liquid carrier. Various other materials can be present as coatings or to otherwise modify the physical form and properties of the dosage unit. For instance, tablets, pills, or capsules can be coated with shellac, sugar, or both. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, ice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

In one alternative, a sustained-release formulation is used. Sustained-release formulations are well-known in the art. For example, they can include the use of polysaccharides such as xanthan gum and locust bean gum in conjunction with carriers such as dimethylsiloxane, silicic acid, a mixture of mannans and galactans, xanthans, and micronized seaweed, as recited in U.S. Pat. No. 6,039,980 to Baichwal, incorporated herein by this reference. Other sustained-release formulations incorporate a biodegradable polymer, such as the lactic acid-glycolic acid polymer recited in U.S. Pat. No. 6,740,634 to Saikawa et al., incorporated herein by this reference. Still other sustained-release formulations incorporate an expandable lattice that includes a polymer based on polyvinyl alcohol and polyethylene glycol, as recited in U.S. Pat. No. 4,428,926 to Keith, incorporated herein by this reference. Still other sustained-release formulations are based on the Eudragit™ polymers of Rohm & Haas that include copolymers of acrylate and methacrylates with quaternary ammonium groups as functional groups as well as ethylacrylate-methylmethacrylate copolymers with a neutral ester group.

Oral liquid preparations can be in the form of, for example, aqueous or oily suspensions, solutions, emulsions, syrups, tinctures, or elixirs, or can be presented as a dry product for reconstitution with water or other suitable vehicles before use. Such liquid preparations can contain conventional additives such as suspending agents, for example, sorbitol syrup, methylcellulose, glucose/sugar syrup, gelatin, hydroxymethylcellulose, carboxymethylcellulose, aluminum stearate gel, or hydrogenated edible fats; emulsifying agents, such as lecithin, sorbitan monooleate, or acacia; non-aqueous vehicles (which may include edible oils), for example, almond oil, fractionated coconut oil, oily esters, propylene glycol, or ethyl alcohol; or preservatives, for example, methylparaben, propylparaben, or sorbic acid. The preparations can also contain buffer salts, flavoring, coloring, or sweetening agents (e.g., mannitol) as appropriate.

One skilled in the art recognizes that the route of administration is an important determinant of the rate of efficiency of absorption. For example, the alimentary route, e.g., oral, rectal, sublingual, or buccal, is generally considered the safest route of administration. The delivery of the drugs into the circulation is slow, thus eliminating rapid high blood levels of the drugs that could potentially have adverse acute effects. Although this is considered the safest route of administration, there are several disadvantages. One important disadvantage is that the rate of absorption varies, which is a significant problem if a small range in blood levels separates a drug's desired therapeutic effect from its toxic effect, i.e., if the drug has a relatively low therapeutic index. Also, patient compliance is not always ensured, especially if the rectal route of administration is chosen or if oral administration is perceived by the patient as unpleasant. Furthermore, with oral administration, extensive hepatic metabolism can occur before the drug reaches its target site. Another route of administration is parenteral, which bypasses the alimentary tract. One important advantage of parenteral administration is that the time for the drug to reach its target site is decreased, resulting in a rapid response, which is essential in an emergency. Furthermore, parenteral administration allows for delivery of a more accurate dose. Parenteral administration also allows for more rapid absorption of the drug, which can result in increased adverse effects. Unlike alimentary administration, parenteral administration requires a sterile formulation of the drug and aseptic techniques are essential. The most significant disadvantage to parenteral administration is that it is not suitable for insoluble substances. In addition to alimentary and parenteral administration routes, topical and inhalation administrations can be useful. Topical administration of a drug is useful for treatment of local conditions; however, there is usually little systemic absorption. Inhalation of a drug provides rapid access to the circulation and is the common route of administration for gaseous and volatile drugs, or drugs that can be vaporized or nebulized. It is also a desired route of administration when the targets for the drug are present in the pulmonary system.

When compounds are formulated for parenteral administration, e.g., formulated for injection via the intravenous, intramuscular, subcutaneous, intralesional, or intraperitoneal routes, many options are possible. The preparation of an aqueous composition that contains an effective amount of the β-adrenergic inverse agonist as an active ingredient will be known to those of skill in the art. Typically, such compositions can be prepared as injectables, either as liquid solutions and/or suspensions. Solid forms suitable for use to prepare solutions and/or suspensions upon the addition of a liquid prior to injection can also be prepared. The preparations can also be emulsified.

The pharmaceutical forms suitable for injectable use include sterile aqueous solutions and/or dispersions; formulations including sesame oil, peanut oil, synthetic fatty acid esters such as ethyl oleate, triglycerides, and/or aqueous propylene glycol; and/or sterile powders for the extemporaneous preparation of sterile injectable solutions and/or dispersions. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. In all cases the form must be sterile and/or must be fluid to the extent that the solution will pass readily through a syringe and needle of suitable diameter for administration. It must be stable under the conditions of manufacture and storage and must be preserved against the contaminating action of microorganisms, such as bacteria or fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and/or mixtures thereof and/or in oils. Under ordinary conditions of storage and use, these preparations contain a preservative to prevent the growth of microorganisms. Suitable non-sensitizing and non-allergenic preservatives are well known in the art.

The carrier can also be a solvent and/or dispersion medium containing, for example, water, ethanol, a polyol (for example, glycerol, propylene glycol, and/or liquid polyethylene glycol, and/or the like), suitable mixtures thereof, and/or vegetable oils. The proper fluidity can be maintained for example, by the use of a coating, such as lecithin, by the maintenance of a suitable particle size in the case of a dispersion, and/or by the use of surfactants. The prevention of the action of microorganisms can be brought about by the inclusion of various antibacterial and/or antifungal agents, for example, parabens, chlorobutanol, phenol, sorbic acid, or thimerosal. In many cases it will be preferable to include isotonic agents, for example, sugars or sodium chloride. In many cases, it is preferable to prepare the solution in physiologically compatible buffers such as Hanks's solution, Ringer's solution, or physiological saline buffer. Prolonged absorption of the injectable compositions can be brought about by the use in the compositions of agents delaying absorption, for example, aluminum monostearate and/or gelatin.

Sterile injectable solutions are prepared by incorporating the active compounds in the required amount in the appropriate solvent with several of the other ingredients enumerated above, as required, followed by sterilization. Sterilization is typically performed by filtration. Generally, dispersions are prepared by incorporating the various sterilized active ingredients into a sterile vehicle which contains the basic dispersion medium and/or the other required ingredients. In the case of sterile powders for the preparation of sterile injectable solutions, the preferred methods of preparation are vacuum-drying and/or freeze-drying techniques that yield a powder of the active ingredients plus any additional desires ingredients from a previously sterile-filtered solution thereof. The preparation of more concentrated or highly concentrated solutions for direct injection is also contemplated, where the use of dimethyl sulfoxide (DMSO) as solvent is envisioned to result in extremely rapid penetration, delivering high concentrations of the active agents to a small area if desired.

For parenteral administration in an aqueous solution, for example, the solution should be suitably buffered if necessary and/or the liquid diluent first rendered isotonic with sufficient saline, glucose, or other tonicity agent. These particular aqueous solutions are especially suitable for intravenous, intramuscular, subcutaneous, or intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected into the proposed site of infusion (see, e.g., "Remington's Pharmaceutical Sciences" (15th ed.), pp. 1035-1038, 1570-1580). Some variation in dosage will necessarily occur depending on the condition of the subject being treated. The person responsible for administration will, in any event, determine the appropriate dose for the individual subject. Compounds and compositions according to the invention can also be formulated for parenteral administration by bolus injection or continuous infusion and can be presented in unit dose form, for instance as ampoules, vials, small volume infusions, or pre-filled syringes, or in multi-dose containers with an added preservative.

Another route of administration of compositions according to the present invention is nasally, using dosage forms such as nasal solutions, nasal sprays, aerosols, or inhalants. Nasal solutions are usually aqueous solutions designed to be administered to the nasal passages in drops or sprays. Nasal solutions are typically prepared so that they are similar in many respects to nasal secretions, so that normal ciliary action is maintained. Thus, the aqueous nasal solutions usually are isotonic and/or slightly buffered in order to maintain a pH of from about 5.5 to about 6.5. In addition, antimicrobial preservatives, similar to those used in ophthalmic preparations, and/or appropriate drug stabilizers, if required, can be included in the formulation. Various commercial nasal preparations are known and can include, for example, antibiotics or antihistamines. Spray compositions can be formulated, for example, as aqueous solutions or suspensions or as aerosols delivered from pressurized packs, with the use of a suitable propellant, such as dichlorodifluoromethane, trichlorofluoromethane, dichlorotetrafluoroethane, 1,1,1,2,3,3,3-heptafluoropropane, 1,1,1,2-tetrafluoroethane, carbon dioxide, or other suitable gas.

Aerosol therapy, typically through the route of nasal administration, allows an almost ideal benefit to risk ratio to be achieved because very small doses of inhaled medication provide optimal therapy with minimal adverse effects. However, the therapeutic efficiency of drugs administered by aerosolization depends not only on the pharmacological properties of the drugs themselves, but also on the characteristics of the delivery device. The characteristics of the delivery device influence the amount of drug deposited in the lungs and the pattern of drug distribution in the airways.

Aerosols are airborne suspensions of fine particles. The particles may be solids or liquids. Aerosol particles are heterodisperse (i.e. the particles are of a range of sizes) and aerosol particle size distribution is best described by a log normal distribution. Particles tend to settle (sediment), adhere to each parenchyma are often associated with pulmonary deposition in the peripheral airways in patients with asthma.

In aerosol administration, the nose efficiently traps particles before their deposition in the lung; therefore, mouth breathing of the aerosolized particles is preferred. The aerosolized particles are lost from many sites. Generally, the amount of the nebulized dose reaching the small airways is 15%. In many cases, approximately 90% of the inhaled dose is swallowed and then absorbed from the gastrointestinal tract. The small fraction of the dose that reaches the airways is also absorbed into the blood stream. The swallowed fraction of the dose is, therefore, absorbed and metabolized in the same way as an oral formulation, while the fraction of the dose that reaches the airways is absorbed into the blood stream and metabolized in the same way as an intravenous dose.

When drugs are administered topically (via aerosol delivery to the lungs), the desired therapeutic effects depend on local tissue concentrations, which may not be directly related to plasma drug concentrations. If a sufficiently large dosage of any drug is given, systemic activity can easily be demonstrated with many active agents. This has several implications. First, for the selection of a drug to be inhaled, topical drugs must combine a high intrinsic activity within the target organ and rapid inactivation of the systemically absorbed drug. Secondly, fewer systemic adverse effects should be expected with drugs that have a low oral bioavailability (whether due to poor gastrointestinal absorption or high first-pass hepatic metabolism). Because most inhaled drugs are administered at a low dosage and have a low oral bioavailability, plasma concentrations of these drugs are much lower than after oral administration.

Furthermore, factors influencing pulmonary absorption should be considered. It was recently demonstrated that terbutaline was absorbed through the lung more rapidly in healthy smokers than in healthy nonsmokers. This may other (coagulate), and adhere to structures such as tubing and mucosa (deposit). The particles delivered by aerosol can be conveniently characterized on the basis of their aerodynamic behavior. One parameter is the mass median aerodynamic diameter (MMAD). By definition, a particle distribution with an MMAD of 1 µM has the same average rate of settling as a droplet of unit density and 1 µM diameter.

The size of an aerosol particle, as well as variables affecting the respiratory system, influence the deposition of inhaled aerosols in the airways. On one hand, particles larger than 10 µM in diameter are unlikely to deposit in the lungs. However, particles smaller than 0.5 µM are likely to reach the alveoli or may be exhaled. Therefore, particles that have a diameter of between 1 µM and 5 µM are most efficiently deposited in the lower respiratory tract. Particles of these sizes are most efficient for the delivery of therapeutic agents for the treatment of airway diseases and conditions, such as infections associated with the occurrence of biofilms.

The percentage of the aerosol mass contained within respirable droplets (i.e., droplets with a diameter smaller than 5 µM), depends on the inhalation device being used. Slow, steady inhalation increases the number of particles that penetrate the peripheral parts of the lungs. As the inhaled volume is increased, the aerosol can penetrate more peripherally into the bronchial tree. A period of breath-holding, on completion of inhalation, enables those particles that have penetrated to the lung periphery to settle into the airways via gravity. Increased inspiratory flow rates, typically observed in patients with acute asthma, result in increased losses of inhaled drug. This occurs because aerosol particles impact in the upper airway and at the bifurcations of the first few bronchial divisions. Other factors associated with pulmonary airway disease may also alter aerosol deposition. Airway obstruction and changes in the pulmonary Ultrasonic nebulizers produce an aerosol by vibrating liquid lying above a transducer at frequencies of about 1 mHz. This produces a cloud of particles that is carried out of the device to the patient by a stream of air. Aerosols varying in quantity, size and distribution of panicles can be produced by nebulizers, depending upon the design of the nebulizers and how it is operated. It should be noted that not all nebulizers have the required specifications (MMAD, flow, output) to provide optimum efficacy. A recent study compared the lung deposition from 4 nebulizers in healthy volunteers and showed that median lung aerosol deposition, expressed as percentages of the doses initially loaded into the nebulizers, ranged from 2 to 19%. Nebulized aerosols are particularly useful for children under 5 years of age and in the treatment of severe asthma where respiratory insufficiency may impair inhalation from an MDI or dry powder inhaler. To minimize adverse effects, pH and osmolarity of the nebulized solution should be controlled.

Metered dose inhalers (MDIs), because of their convenience and effectiveness, are probably the most widely used therapeutic aerosol used for inhaled drug delivery to outpatients. Most MDIs in current use contain suspensions of drug in propellant. There are 2 major components of an MDI: (i) the canister, a closed plastic or metal cylinder that contains propellant, active medication, and the metering chamber; and (ii) the actuator, a molded plastic container that holds the canister and directs the released aerosol towards the patient's airway.

Propellant mixtures are selected to achieve the vapor pressure and spray characteristics desired for optimal drug delivery. Chlorofluorocarbons were previously used, but non-chlorinated propellants are now employed because of environmental concerns. Finely divided particles of drug, usually less than 1 µM, are suspended in the pressurized (liquefied) propellant. To prevent the drug from coagulating, a surface active agent such as sorbitan oleate, lecithin or oleic acid is typically added; other surface active agents are known in the art affect the onset of action of the drug. It has also been found that the bioavailability of inhaled salbutamol in 10 patients with cystic fibrosis was greater than that in healthy adults. One proposed mechanism for this difference in bioavailability is that the chronically diseased tracheobronchial tree in patients with cystic fibrosis results in higher permeability of salbutamol in this tissue. However, data are limited in this area, and further investigation is required to substantiate these claims.

Finally, the absolute pulmonary bioavailability of inhaled drugs is difficult to assess because blood concentrations are low, and pulmonary and oral absorption should be discriminated for pulmonary bioavailability to be determined as accurately as possible. Charcoal can be used to adsorb the swallowed fraction of inhaled terbutaline to discriminate the pulmonary absorption of the drug. Recently, it was shown that a urine collection during the 30 minutes after inhalation of salbutamol represents the amount of drug delivered to the lungs. This technique may be applicable for the determination of bioavailability of other inhaled drugs. Other techniques for the determination of bioavailability of inhaled drugs are also known in the art; these include pharmacodynamic methods using $FEV_1$ measurements, lung deposition studies using radiolabeled formulations, or pharmacokinetic studies using predominantly urinary excretion measurements.

Therapeutic aerosols are commonly produced by atomization of liquids within jet nebulizers or by vibration of a standing pool of liquid (ultrasonic nebulization). Preformed aerosols may also be administered. Examples of the latter include MDIs and dry powder devices. Whatever delivery device is used, patients should be taught to use it correctly.

All jet nebulizers work via a similar operating principle, represented by the familiar perfume atomizer. A liquid is placed at the bottom of a closed container, and the aerosol is generated by a jet of air from either a compressor or a compressed gas cylinder passing through the device. Metering chambers ordinarily contain 25 to 100 µL. The contents of the metering chamber are released when the canister is depressed into the actuator. Almost instantaneously, the propellants begin to evaporate, producing disintegration of the discharged liquid into particles that are propelled forward with great momentum. For optimal pulmonary drug deposition, the medication should be released at the beginning of a slow inspiration that lasts about 5 seconds and is followed by 10 seconds of breath-holding. Several inhalation aids have been designed to improve the effectiveness of a MDI. These are most useful in patients who have poor hand-to-breath coordination. A short tube (e.g. cones or spheres) may direct the aerosol straight into the mouth or collapsible bags may act as an aerosol reservoir holding particles in suspension for 3 to 5 seconds, during which time the patient can inhale the drug. However, when any of these devices is used, aerosol velocity upon entering the oropharynx is decreased and drug availability to the lungs and deposition in the oropharynx is decreased.

Dry powder inhalers have been devised to deliver agents to patients who have difficulty using an MDI (e.g. children and elderly patients). In general, the appropriate dosage is placed in a capsule along with a flow aid or filler such as large lactose or glucose panicles. Inside the device, the capsule is initially either pierced by needles (e.g. Spinhaler®) or sheared in half (e.g. Rotohaler®). During inhalation the capsule rotates or a propeller is turned, creating conditions that cause the contents of the capsule to enter the inspired air and be broken up to small particles suitable for delivery to the airways. The energy required to disperse the powder is derived from the patient's inspiratory effort. Recently, more convenient multidose dry powder inhalers have been introduced (e.g. Diskhaler®, Turbuhaler®). Potential problems associated with dry powder inhalers include esophageal irritation and, consequently, cough due to the direct effect of powder in airways. Furthermore, the walls of the capsule may be coated with drug as a result of either failure of the capsule to release the drug or failure of the aggregated powder to break up. This may cause virtually the entire drug to be deposited in the mouth. These powder devices do not contain chlorofluorocarbons and may provide an alternative to MDIs.

To ensure maximal effects from inhaled drugs, both the pharmacological characteristics of the drugs and the device used to aerosolize the drugs should be considered. For a number of active agents, different formulations, with different pulmonary disposition techniques, are available, such as for MDI administration, for administration with a dry powder inhaler, or a solution for nebulization. A unit dose from a dry powder inhaler is twice that release from an MDI, but they have equivalent bronchodilatory effects. The characteristics of the devices vary. For a metered-dose inhaler, typically 12-40% of the dose is deposited in the lung, but up to 80% in the oropharynx. When an MDI is used with a spacer, typically about 20% of the dose is deposited in the lung, but only up to 5% in the oropharynx; thus, the use of a spacer can reduce the proportion of the drug that is deposited in the oropharynx. For a dry powder inhaler, typically 11-16% of the dose is deposited in the lung and 31-72% in the oropharynx. For a nebulizer, typically 7-32% of the dose is deposited in the lung and 1-9% is deposited in the oropharynx. One of ordinary skill in the art can ensure that the proper inhalation therapy device is used and can prepare suitable instructions. Considerations for the use of inhalation therapy are described in A. M. Tabaret & B. Schmit, "Pharmacokinetic Optimisation of Asthma Treatment," Clin. Pharmacokinet. 26: 396-418 (1994), incorporated herein by this reference.

The method of treating the airway infection can further comprise the administration of an antibiotic that is effective in the treatment of *M. pneumoniae* in a quantity effective to exert a bactericidal action against *M. pneumoniae*, the antibiotic being administered by a route other than route of administration of the composition according to the present invention. Suitable antibiotics are described above. If the composition according to the present invention includes an antibiotic, the antibiotic that is administered by the route other than route of administration of the composition according to the present invention can be the same antibiotic included in the composition or can be a different antibiotic. If the composition according to the present invention does not include an antibiotic, the antibiotic administered by the additional route can be any antibiotics described above as being effective in the treatment of the infection. The route of administration, dose administered, and the frequency of administration can be determined by one of ordinary skill in the art by reference to the parameters described above, such as the subject's age, size, weight, and health, the extent of the infection, the bacterium causing the infection, the presence of other conditions such as allergic reactions that can complicate the infection, and the therapeutics or combination of therapeutics selected for administration, as well as variables such as liver and kidney function that affect the pharmacokinetics of administered therapeutics, and the properties of the antibiotic such as its molecular weight and relative degree of hydrophobicity or hydrophilicity, as well as its susceptibility to hydrolysis in the digestive tract. Typically, administration of the antibiotic administered by the additional route is by the oral or parenteral route; if parenteral, typically the antibiotic is administered intramuscularly. In some cases of severe infection, intravenous administration can be required. Information on specific antibiotics and optimum routes of administration can be found, for example, in J. G. Hardman & L. E. Limbird, eds., "Goodman & Gilman's The Pharmacological Basis of Therapeutics" (10th ed., McGraw-Hill, New York, 2001), the relevant portions of which are incorporated herein by this reference.

Advantages of the Invention

The present invention provides a safe and effective means for treating airway infection and particularly those infections caused by *Mycoplasma pneumoniae*. Compositions and methods according to the present invention, in removing bacteria-laden biofilm, not only provide for more effective treatment of such infections, but also prevent recurrence of the infections. Compositions and methods according to the present invention are suitable for use with other treatment modalities, such as antibiotic administration, and do not cause inflammation or other side effects.

Accordingly, compositions and methods according to the present invention possess industrial applicability for the preparation of medicaments for the treatment of infections and especially for the treatment of infections caused by *M. pneumoniae.*

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also forms part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of ordinary skill in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

What is claimed is:

1. A method of dissolving biofilm present in an airway infection comprising administering a therapeutically effective amount of a composition to an individual in need thereof, wherein the composition comprises effective amounts of lysozyme, lactoferrin and at least one enzyme that catalyzes the hydrolysis of a bond that connects two monosaccharides in a polysaccharide or that connects a monosaccharide with a protein molecule in a glycoprotein sufficient to break down biofilm in airway passages, wherein the composition is formulated to target the biofilm.

2. The method of claim 1, wherein the composition further comprises at least one steroid selected from the group consisting of hydrocortisone, beclomethasone, budesonide, ciclesonide, flunisolide, fluticasone, methylprednisone, prednisolone, prednisone, and triamcinolone.

3. The method of claim 1, wherein the composition thither comprises a pharmaceutically acceptable carrier suitable for administration into the airway passages selected from the group consisting of water, ethanol and a polyol.

4. The method of claim 3, wherein the pharmaceutically acceptable carrier suitable for administration into the airway passages includes propylene glycol, glycerol, or tripropylene glycol.

5. The method of claim 1, wherein the composition further comprises an amount of an antibiotic that is effective against bacteria underlying the airway infection.

6. The method of claim 5, wherein the antibiotic is delivered in a quantity effective to exert a bactericidal action against *Mycoplasma pneumoniae*, further wherein the antibiotic is selected from the group consisting of amikacin, ticarcillin, piperacillin, mezlocillin, ceftazidime, cefepime, ciprofloxacin, tobramycin, aztreonam, imipenem, and meropenem.

7. The method of claim 1, wherein the composition further comprises at least one peroxidase in a quantity sufficient to exert a bactericidal action.

8. The method of claim 7, wherein the at least one peroxidase is selected from the group consisting of lactoperoxidase, myeloperoxidase, horseradish peroxidase, eosinophil peroxidase, and glutathione peroxidase.

9. The method of claim 1, wherein the composition further comprises at least one substrate that can be converted to an ion with bactericidal properties by the enzymatic action of the peroxidase in a quantity such that an effective concentration of the ion with bactericidal properties is produced by the catalytic action of the peroxidase.

10. The method of claim 9, wherein the at least one substrate is an alkali metal salt of thiocyanate, iodate, or chlorate.

11. The method of claim 9, wherein the composition further comprises an aminohexose in a quantity effective to increase the yield or accumulation of oxidized anionic biocidal agent.

12. The method of claim 1, wherein the composition further comprises an oxidase selected from the group consisting of glucose oxidase, galactose oxidase, urate oxidase, choline oxidase, D-amino acid oxidase, D-glutamate oxidase, glycine oxidase, glycolic oxidase, L-sorbose oxidase, alcohol oxidase, and amine oxidase.

13. The method of claim 1, wherein the composition is delivered to the individual via a route of administration selected from the group consisting of oral, sublingual, buccal, and nasal.

14. A method of treating an airway infection in the lung of an individual having a quantity of biofilm in an airway passage associated with the airway infection, the method comprising:
    administering a therapeutically effective amount of a composition to the individual, wherein the composition comprises effective amounts of lysozyme, lactoferrin, and at least one enzyme that catalyzes the hydrolysis of a bond that connects two monosaccharides in a polysaccharide or that connects a monosaccharide with a protein molecule in a glycoprotein sufficient to break down the biofilm in the airway passage.

15. The method of claim 14, wherein the airway infection is caused by *Mycoplasma pneumoniae*.

16. The method of claim 14, wherein the composition further comprises an antibiotic that targets a bacteria associated with the airway infection and is administered to the individual by a route of administration other than nasal.

17. A method of treating an airway infection characterized by a biofilm formation in an individual suffering therefrom, the method comprising administering a therapeutically effective amount of a formulation to the individual, wherein the formulation comprises lysozyme, lactoferrin, and lactoperoxidase in amounts effective to dissolve the biofilm formation.

18. The method of claim 17, further comprising, after administering the formulation, administering an antibiotic to the individual.

* * * * *